United States Patent
Nishio et al.

(10) Patent No.: US 8,436,622 B2
(45) Date of Patent: May 7, 2013

(54) METHOD FOR MEASUREMENT OF CONTENT OF WATER OR ORGANIC ACID IN POLAR ORGANIC SOLVENT, AND APPARATUS FOR THE METHOD

(75) Inventors: Yuji Nishio, Kyoto (JP); Yasukazu Iwamoto, Kyoto (JP)

(73) Assignee: Horiba, Ltd., Kyoto (JP)

( * ) Notice: Subject to any disclaimer, the term of this patent is extended or adjusted under 35 U.S.C. 154(b) by 364 days.

(21) Appl. No.: 12/743,922

(22) PCT Filed: Dec. 26, 2008

(86) PCT No.: PCT/JP2008/073837
§ 371 (c)(1),
(2), (4) Date: May 20, 2010

(87) PCT Pub. No.: WO2009/084675
PCT Pub. Date: Jul. 9, 2009

(65) Prior Publication Data
US 2010/0259271 A1    Oct. 14, 2010

(30) Foreign Application Priority Data
Dec. 27, 2007 (JP) ................................. 2007-335542

(51) Int. Cl.
G01N 27/02 (2006.01)
G01N 27/00 (2006.01)

(52) U.S. Cl.
USPC .................... 324/444; 324/71.1; 324/71.5

(58) Field of Classification Search .............. 324/444, 324/71.1, 71.5
See application file for complete search history.

(56) References Cited

U.S. PATENT DOCUMENTS
5,340,541 A * 8/1994 Jackson et al. .................. 422/75
2006/0102935 A1 * 5/2006 Yitzchaik et al. ............. 257/253

FOREIGN PATENT DOCUMENTS
| EP | 0307973 A2 * | 3/1989 |
| JP | 06-160319 | 6/1994 |
| JP | 06-201634 | 7/1994 |
| JP | 06-317552 | 11/1994 |
| JP | 2001-033423 | 2/2001 |
| JP | 2002-181776 | 6/2002 |
| JP | 2008-256488 | 10/2008 |
| JP | 2009-025124 | 2/2009 |

* cited by examiner

Primary Examiner — Amy He

(57) ABSTRACT

Disclosed are a measurement method and a measurement apparatus both of which can measure the content of water or an organic acid in a polar organic solvent with high accuracy even when water or the organic acid is contained in the polar organic solvent at a low content. The content of water or an organic acid in a polar organic solvent can be measured by using, as a work electrode, an ISFET electrode in which a thin film comprising an oxide or nitride of a metal or metalloid element belonging to Groups 3 to 15 is formed on a gate.

8 Claims, 4 Drawing Sheets

METHOD FOR MEASUREMENT OF CONTENT OF WATER OR ORGANIC ACID IN POLAR ORGANIC SOLVENT, AND APPARATUS FOR THE METHOD

RELATED APPLICATIONS

The present application claims priority from PCT/JP2008/073837 filed on Dec. 26, 2008 which claims priority from Japanese Patent Application 2007-335542 filed on Dec. 27 2007.

TECHNICAL FIELD

The present invention relates to a measurement method and a measurement apparatus capable of measuring a content of water or organic acid in a polar organic solvent with high accuracy even if the water or organic acid is contained in the polar organic solvent at a low concentration.

BACKGROUND ART

In recent years, attention has been paid to renewable biological fuel such as bioethanol (biomass ethanol) because global warming is being recognized as a serious issue and cost of fossil fuel is rising.

The bioethanol is produced by fermenting and distilling biomass such as sugarcane or corn. However, if water is mixed into ethanol, combustion efficiency deteriorates. Due to this, it is necessary to manage a water content strictly in a process of producing the bioethanol.

Patent Document 1 discloses a method of measuring a water content in a nonaqueous solvent using conductive polymer which electric conductivity reversibly increases when the conductive polymer is hydrated using water. However, with the method disclosed in the Patent Document 1, if an electrolyte other than the water is mixed into the nonaqueous solvent as impurity, measurement error tends to occur due to influence of mixture of the electrolyte.

Furthermore, as a method of measuring a water content in an organic solvent or the like, there is known Karl-Fischer method of measuring a water content using a Karl Fischer reagent containing iodine, sulfur dioxide, a base, alcohol and the like and reacting with water selectively and quantitatively. While there are known, as types of the Karl-Fischer method, coulometric titration and volumetric titration, apparatuses for the both methods are large in size and complicated.

Moreover, the coulometric titration that is an electrochemical method out of the types of the Karl-Fischer method is intended to indirectly measure a water content by adding a sample to an electrolytic solution containing the Karl-Fischer reagent, subjecting the sample-added electrolytic solution to electrolytic oxidation, calculating a quantity of electricity required for the electrolytic oxidation based on Faraday's law from a quantity of the iodine generated according to a reaction represented by a formula "$2I^- - 2e \rightarrow I_2$", and reducing the quantity of electricity to the water content according to "1 mg of water=10.71 coulomb".

Patent Document 1: Japanese Unexamined Patent Publication No. 1994-160319

DISCLOSURE OF THE INVENTION

Problems to be Solved by the Invention

An object of the present invention is, therefore, to provide a measurement method and a measurement apparatus that is simple and capable of accurately measuring a content of water or organic acid in a polar organic solvent even if the water or organic acid is contained in the polar organic solvent at low concentration.

Means to Solve the Problems

That is, a measurement method according to the present invention is a method for measuring a content of water or organic acid in a polar organic solvent using, as a working electrode, an ISFET electrode, with a membrane made of an oxide or a nitride of an element selected from Groups 3 to 15 metal or metalloid elements formed on a gate of the ISFET electrode.

The polar organic solvent as a measurement target in the present invention is a solvent having a high dielectric constant and high polarity. Examples of the polar organic solvent include alcohol such as ethanol, N,N-dimethylformamide (DMF), dimethyl sulfoxide (DMSO), and hexamethyl phosphoramide (HMPA). Among them, examples of the alcohol include ethanol, n-butanol, isopropyl alcohol, and alcohol produced by alcoholic fermentation of glycerol. The measurement method according to the present invention is particularly preferably used to measure a content of water or organic acid in so-called bioethanol obtained by fermenting and distilling biomass such as sugarcane or corn.

The ISFET electrode consists of an Ion Sensitive Field Effect Transistor. If a sample solution contacts with an ion-sensitive membrane on a gate of the ISFET, a phase boundary potential is generated according to activity of hydrogen ions in the sample solution. If the membrane made of the oxide or nitride of the element selected from among the Groups 3 to 15 metal or metalloid elements such as $TiO_2$, $Ta_2O_5$, $Si_3N_4$, more preferably a membrane made of $Ta_2O_5$ is formed on a gate of the ISFET, the ISFET electrode functions as a sensor sensitive to hydrogen ions. The Groups 3 to 15 metal or metalloid elements mean metal or metalloid elements that are possibly in an electronic state of containing three or more cations.

According to the present invention, the content of water or organic acid is measured by detecting hydrogen ions directly in the polar organic solvent using the ISFET electrode. In this respect, although being the same electrochemical method as the coulometric titration as one type of the Karl-Fischer method, the present invention clearly differs from the coulometric titration.

A pH glass electrode similarly directly detects hydrogen ions. However, the pH glass electrode has the following problems. A hydrated gel layer is generated on a surface of a sensitive glass membrane, thereby forming a silanol ion-exchange site. Since a potential difference is generated by a concentration gradient of hydrogen ions formed through this site, a pH can be measured. Nevertheless, a certain amount of water is necessary to form the hydrated gel layer on the surface of the sensitive glass membrane. If the pH glass electrode is immersed in the polar organic solvent, the hydrated gel layer is dehydrated. This makes the ion-exchange site unstable and deteriorates response and stability of the pH glass electrode. Further, a sufficient response speed is not ensured for the pH glass electrode because the hydrated glass layer of the pH glass electrode is relatively thick.

A hydrated gel layer of the ISFET electrode used as the work electrode in the present invention, by contrast, is quite thin. Due to this, the hydrated gel layer can be generated easily even by a small amount of water, and the content can be measured with high response speed and high sensitivity.

FIG. 4 is a graph comparing response of an ISFET electrode on a gate of which a membrane made of $Ta_2O_5$ is formed with that of a pH glass electrode. As shown in FIG. 4, when the solvent in which the ISFET electrode is immersed was substituted from pH7 buffer to ethanol, the ISFET electrode was made stable in one minute. When the solvent in which the ISFET electrode is immersed was substituted from the ethanol to the pH7 buffer, the ISFET electrode had good response. On the other hand, when the solvent in which the pH glass electrode is immersed was substituted from the pH7 buffer to the ethanol, the pH glass electrode was not made stable even after 15 minutes.

While the polar organic solvent such as ethanol slightly dissociates, the water is far higher in a dissociation constant than the polar organic solvent. Due to this, by measuring a hydrogen ion concentration in the polar organic solvent, it is possible to evaluate a water content in the polar organic solvent almost accurately. Likewise, organic acid such as acetic acid is far higher in the dissociation constant than the polar organic solvent such as ethanol. Due to this, it is possible to evaluate a content of a slight amount of organic acid mixed in the polar organic solvent almost accurately. It is to be noted that the organic acid is an organic compound emitting protons such as acetic acid or formic acid, and needs to be far higher in the dissociation constant than the polar organic acid and is preferably higher in the dissociation constant than the water.

It is to be noted that the dissociation constant is defined by a product (an ion product) between an acid and a base in a pure solvent. For example, while the dissociation constant (ion product) of water is $10^{-14}$, dissociation constants (ion products) of ethanol and methanol that are typical examples of the polar organic solvent are $10^{-19.1}$ and $10^{-16.7}$ (at 25° C.)

From these, a median that is an equivalent point between the acid and the base of the water is about 7 whereas the median of the ethanol is near 10, that is, offset to alkali side with respect to that of the water.

If water is added to ethanol, the hydrogen ion concentration changes greatly in the sample and the median shifts to an acid side with respect to the ethanol. By grasping this change using the ISFET, it is possible to evaluate even a content of a small amount of water mixed in the polar organic solvent almost accurately.

Likewise, the formic acid (dissociation constant: $10^{-6.2}$ (at 25° C.)) or the acetic acid (dissociation constant: $10^{-4.8}$ (at 25° C.)) as an organic acid is far higher in the dissociation constant than the polar organic solvent such as ethanol. By adding the organic acid such as the formic acid or acetic acid to the polar organic solvent such as ethanol, the median shifts similarly.

In case of the organic acid, in particular, as described above, the median of the organic acid is near 2 to 3, so a median difference of the organic acid is greater than that of the polar organic acid. If the median difference is greater, the potential difference to be measured by the ISFET becomes higher. Due to this, even if a content of the organic acid is very low, a width of potential change is large. Therefore, it is possible to evaluate the content of a small amount of the organic acid accurately.

In the present invention, if the content of the water or organic acid is continuously measured, a flow injection analysis method may be used. If continuous measurement can be made, it is appropriate for quality management and the like of bioethanol.

A measurement apparatus for carrying out the measurement method according to the present invention is not limited to a specific apparatus. However, the measurement apparatus needs to include, as a working electrode, an ISFET electrode, with a membrane made of an oxide or a nitride of an element selected from among Groups 3 to 15 metal or metalloid elements such as $TiO_2$, $Ta_2O_5$ or $Si_3N_4$, preferably a membrane made of $Ta_2O_5$ formed on a gate of the ISFET electrode.

It is preferable that a body of the ISFET electrode is made of metal, ceramics, polyphenyl sulfide, fluorine resin such as polytetrafluoroethylene or polyvinylidene fluoride-hexafluoropropylene or glass. The metal, the ceramics, the polyphenyl sulfide, the fluorine resin, the glass or the like has high durability against the organic solvent. Therefore, by constituting the body of the ISFET electrode using such a material, the measurement apparatus can be used for a long time.

The measurement apparatus may include a flow cell. By providing the flow cell, the measurement apparatus can measure continuously using the flow injection analysis method or the like.

Moreover, in the measurement apparatus according to the present invention, the ISFET electrode may include a liquid earth mechanism. If a frictional force is generated between the ISFET electrode and the polar organic solvent serving as a measurement target by stirring the polar organic solvent and a streaming potential is generated, an indication value of the measurement apparatus fluctuates due to influence of the streaming potential. In such a case, if the ISFET electrode includes the liquid earth mechanism, the streaming potential can be eliminated. It is to be noted that a similar effect can be exhibited even if the body of the ISFET electrode is made of metal.

Effects of the Invention

In this way, according to the present invention, it is possible to measure the content of the water or organic acid in the polar organic solvent using the simple apparatus with quite high accuracy in short time. For example, it takes about 10 to 60 minutes to measure the water content in ethanol using the pH glass electrode whereas the water content in ethanol can be measured within one minute using the measurement apparatus according to the present invention. Due to this, it is possible to obtain the measurement apparatus having high performance and capable of making continuous measurement. Moreover, by using a material having durability against a nonaqueous solution as the material of the body of the ISFET electrode, the measurement apparatus can be used for a long time. Furthermore, by applying MEMS technique to the present invention, the measurement apparatus according to the present invention can be made small in size.

DESCRIPTION OF REFERENCE SYMBOLS

Figure 1:
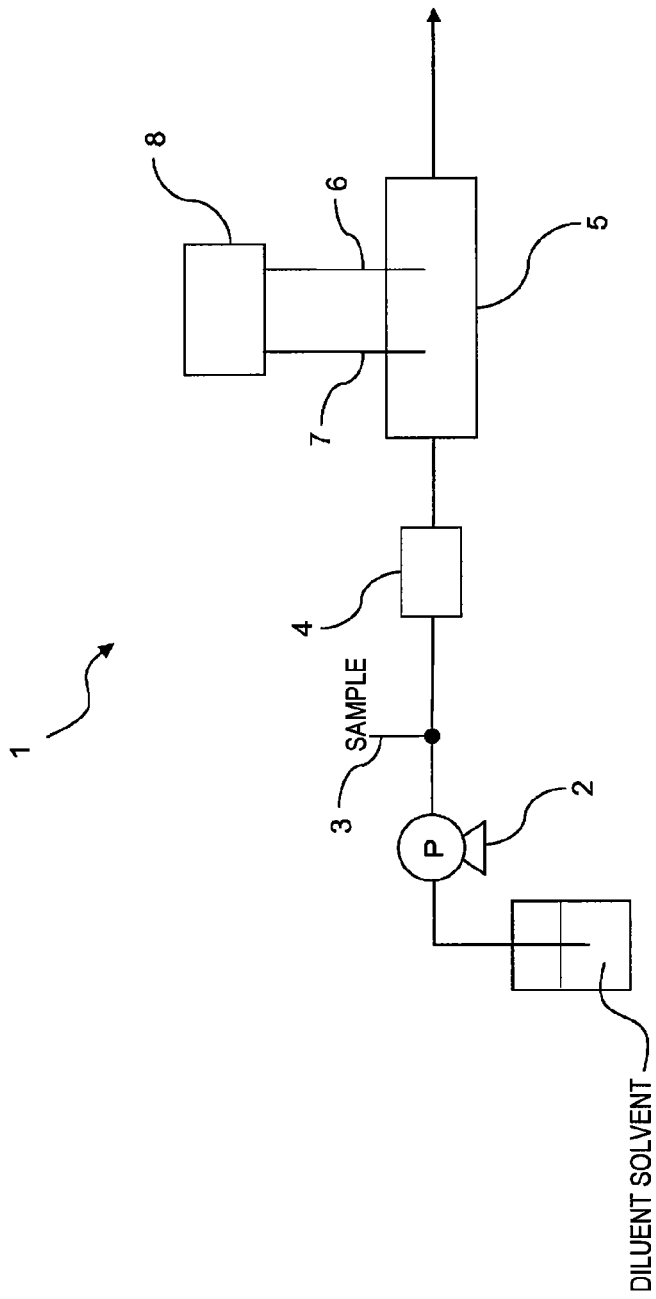
FIG. 1 is a schematic diagram of a measurement apparatus according to an embodiment of the present invention.

1 . . . Water content measurement apparatus
5 . . . Flow cell
6 . . . ISFET electrode
7 . . . Comparison electrode

BEST MODE FOR CARRYING OUT THE INVENTION

A measurement apparatus according to an embodiment of the present invention will be described hereinafter referring to the drawings.

A water content measurement apparatus 1 according to the embodiment of the present invention is a liquid injection apparatus that includes a flow cell as schematically shown in FIG. 1.

Such a water content measurement apparatus 1, which can analyze flow injection, creates a controlled continuous flow using a metering pump or the like, causes reaction, injects a sample and does other things in this flow, detects hydrogen ions in a sample solution, and measures a water content in the sample solution using a water analyzer main body including the flow cell disposed on an end of the water analyzer main body.

The water content measurement apparatus 1 shown in FIG. 1 has a pump 2 followed by an injection port 3 and a stirrer 4 provided upstream of a channel, and has a flow cell 5 including an ISFET electrode 6 and a comparison electrode 7 provided downstream thereof. The water analyzer main body 8 is connected to the ISFET electrode 6 and the comparison electrode 7.

The pump 2 is not limited to a specific type as long as the pump 2 can feed the sample solution to the flow cell 3 at constant velocity, and a liquid chromatography pump, for example, can be used as the pump 2.

The stirrer 4 is not limited to a specific type as long as the stirrer 4 can stir the sample solution, and a device including a rotating stirrer or a magnetic stirrer, for example, can be used as the stirrer 4.

Figure 2:
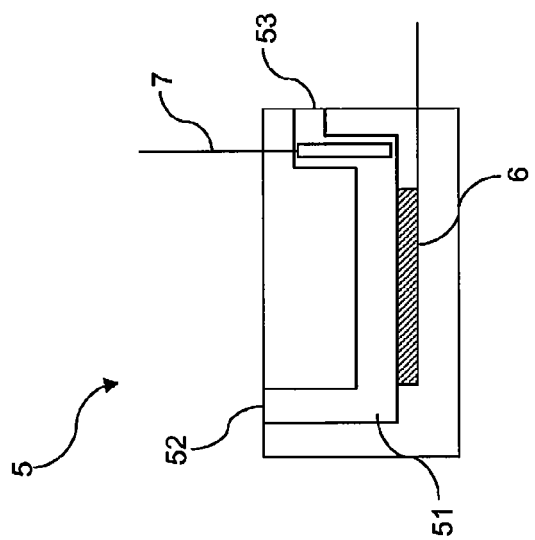
FIG. 2 is a schematic diagram showing a configuration of a flow cell according to the embodiment.

As shown in FIG. 2, the flow cell 5 is configured so that the ISFET electrode 6 and the comparison electrode 7 included therein are exposed into a channel 51 in which the sample solution flows and can contact with the sample solution. The sample solution enters the channel 51 from an inlet 52, flows as indicated by an arrow shown in FIG. 2, and reaches an outlet 53.

Examples of the ISFET electrode 6 include an electrode having a hydrogen ion-sensitive membrane formed on a gate. For example, the examples include an electrode configured so that a membrane made of an oxide or a nitride of an element selected from among Groups 3 to 15 metal or metalloid elements such as $TiO_2$, $Ta_2O_5$ and $Si_3N_4$, preferably a membrane made of $Ta_2O_5$ is formed on a gate of the electrode. In addition, a body of the ISFET electrode 6 is made of metal, ceramics, polyphenyl sulfide, fluorine resin such as polytetrafluoroethylene or polyvinylidene fluoride-hexafluoropropylene, glass or the like.

A packing constituted by a metal ring may be further attached to the body of the ISFET electrode 6 as a liquid earth mechanism.

As the comparison electrode 7, an electrode can be appropriately selected from among well-known electrodes. For example, a standard hydrogen electrode, a silver/silver chloride electrode or a mercury/mercury chloride electrode can be used as the comparison electrode 7. It is to be noted that a problem such as clogging sometimes occurs to a liquid junction because KCl contained in an internal liquid of the comparison electrode 7 is slightly insoluble to a polar organic solvent. Due to this, an electrode including a pinhole liquid junction or a double junction electrode is preferably used as the comparison electrode 7.

The water analyzer main body 8 is a dedicated one integrally including a CPU, an A/D converter, a storage device, input means, a display and the like as a hardware configuration. The CPU and peripherals of the CPU, if necessary, operate based on a program stored in the storage device. The water analyzer main body 8 thereby functions as a measurement data calculation part, a measurement data storage part and the like, calculates a water content from a hydrogen ion concentration detected by the ISFET electrode 6, and displays the calculated water content.

If the water content measurement apparatus 1 according to this embodiment is used to measure a water content in the polar organic solvent, then a sample such as ethanol is added to a diluent solvent for increasing a dielectric constant such as toluene or isopropyl alcohol fed by the pump 2, and the stirrer 4 sufficiently mixes the diluent solvent with the sample. The diluted sample (hereinafter, "sample solution") is fed to the flow cell 5. If the sample solution contacts with the ion-sensitive membrane formed on the gate of the included ISFET electrode 6 in the flow cell 5, a phase boundary potential is generated according to activity of hydrogen ions in the sample solution. This phase boundary potential is measured as a potential difference (voltage) between the ISFET electrode 6 and the comparison electrode 7 using the comparison electrode 7, and calculate a hydrogen ion concentration, the water content is further calculated by a predetermined arithmetic processing, and the calculated water content is displayed on the water analyzer main body 8. The sample solution completed with the measurement is discharged to outside of the water content measurement apparatus 1.

Such a water content measurement apparatus 1 can measure the water content with faster response and with more accuracy by using the ISFET electrode as a work electrode. Further, the water content measurement apparatus 1 can make continuous measurement because the water content measurement apparatus 1 includes the flow cell. Furthermore, the water content measurement apparatus 1 can be used for a long time because a material of the body of the ISFET electrode has durability against a nonaqueous solution.

The present invention is not limited to the above-stated embodiment.

The liquid earth mechanism provided on the ISFET electrode is not limited to the metal ring but a highly-conducting material can be worked into an arbitrary shape and attached to the body of the ISFET electrode.

If the KCl that is the internal liquid contained in the comparison electrode leaks out to the sample solution to make a measurement result unstable, then the ISFET electrode may be provided solely in the flow cell 5 and the comparison electrode may be separately and independently provided downstream of the flow cell 5. By so configuring, it is possible to eliminate influence of leaking of the KCl from the comparison electrode and stabilize the measurement result.

The measurement apparatus according to the present invention may be a batch measurement apparatus. Such a batch measurement apparatus is configured, for example, to include a water analyzer main body and an ISFET electrode and a comparison electrode that are connected to the water analyzer main body. The ISFET electrode and the comparison electrode are immersed in a sample solution filled in a container such as a beaker, and a water content in the sample solution is measured while stirring the sample solution using a magnetic stirrer.

In the batch measurement apparatus, if KCl that is an internal liquid in the comparison electrode leaks out to the sample solution to make a measurement result unstable, the water content may be measured as follows. A diaphragm made of an ion-permeable semipermeable membrane is provided in the container such as the beaker to halve an interior of the container. The sample solution (diluent solvent+sample) is contained in one half and only the diluent solvent is contained in the other half. Only the ISFET electrode is immersed in the sample solution, the comparison electrode and the ISFET electrode are immersed in the diluent solvent, and a difference is calculated between the ISFET electrode in the sample solution and that in the diluent solvent, thereby measuring the water content. By immersing only the ISFET electrode in the sample solution and measuring the water content as stated above, it is possible to eliminate influence of leaking of the KCl from the comparison electrode and stabilize the measurement result.

In another alternative, there is a simple batch measurement apparatus. The simple batch measurement apparatus is configured so that a sample solution is contained in a container having a bottom surface that is a semiconductor wafer and an ISFET formed on the semiconductor wafer, and so that a comparison electrode is immersed in the sample solution, thereby measuring a water content.

As stated above, even an organic acid content in the polar organic solvent can be measured using the ISFET electrode according to a similar principle to that for the water content. Therefore, the water content measurement apparatus 1 according to this embodiment can be also used as an organic acid content measurement apparatus.

Needless to say, various changes and modifications can be made of the present invention without departure from spirit of the present invention.

Figure 3:
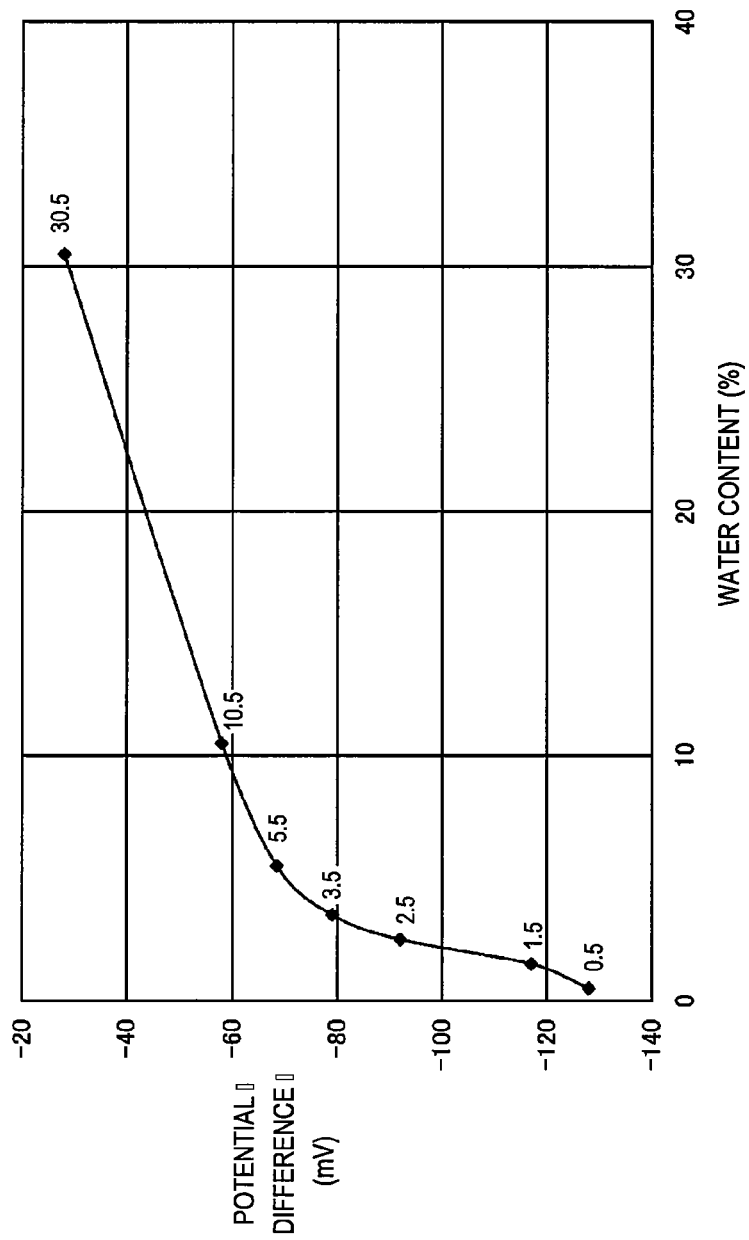
FIG. 3 is a graph showing a result of measuring a low-concentration water content in ethanol.
Figure 4:
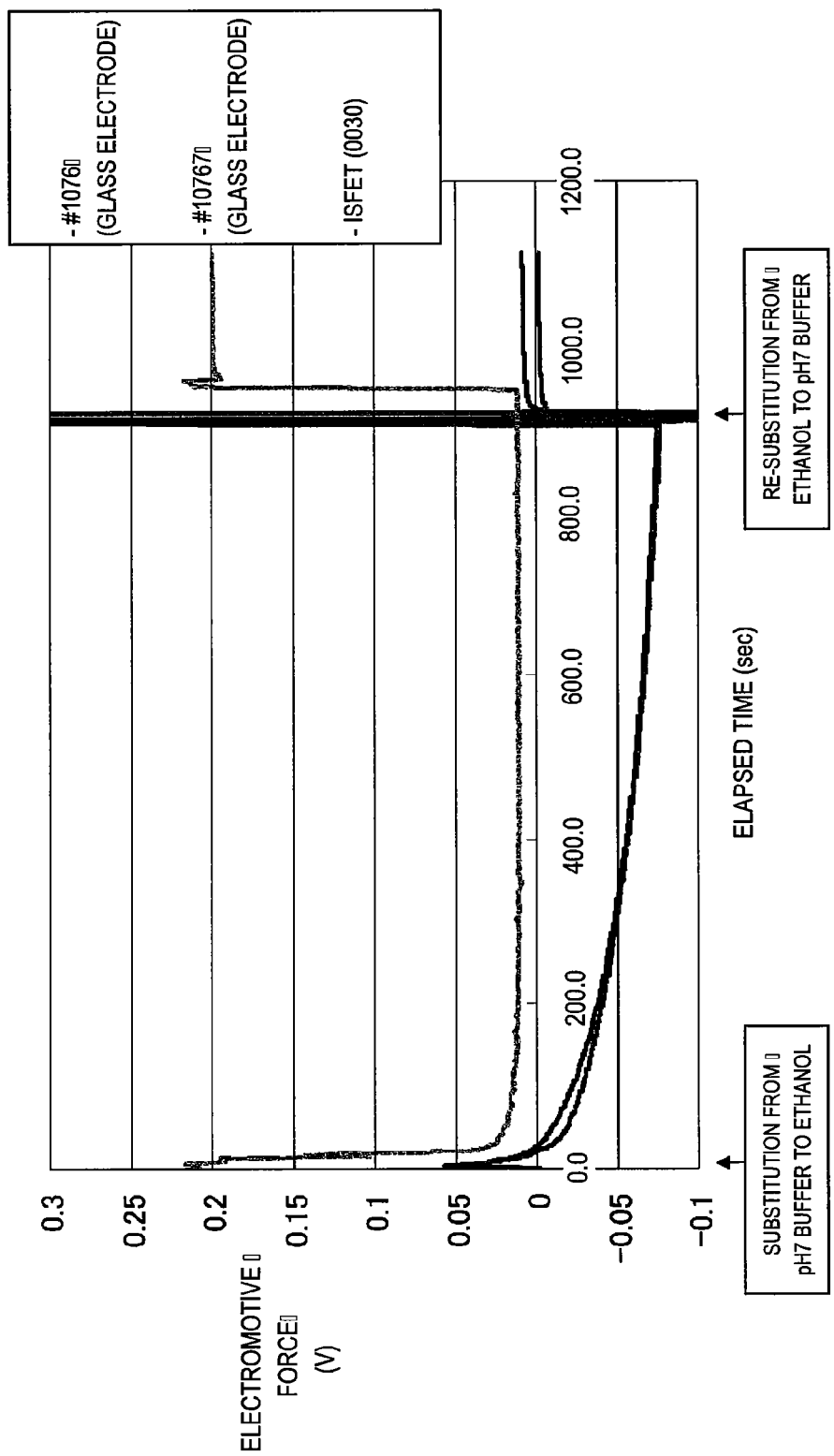
FIG. 4 is a graph comparing response of an ISFET electrode with that of a pH glass electrode.

Meanwhile, the batch measurement apparatus was used as the water content measurement apparatus according to the present invention so as to measure a water content in ethanol while gradually dropping ion-exchange water in one liter of industrial ethanol. As a result, as shown in a graph of FIG. 3, it was confirmed that the water content measurement apparatus according to the present invention can measure low-concentration water in the ethanol with quite high sensitivity.

INDUSTRIAL APPLICABILITY

The present invention can be used to manage a content of water or organic acid in a manufacturing process for alcohol such as bioethanol.

The invention claimed is:

1. A measurement method for measuring a content of water or organic acid in a polar organic solvent based on a hydrogen ion concentration in the polar organic solvent comprising:
    using, as a working electrode, an ISFET electrode, with a membrane made from one of an oxide and a nitride of an element selected from among Groups 3 to 15 metal and metalloid elements being formed on a gate of the ISFET electrode which is sensitive to hydrogen ions; and
    applying the polar organic solvent to the ISFET electrode to have the ISFET electrode detect hydrogen ions in the polar organic solvent to provide a signal from the ISFET electrode representative of a content of one of water and the organic acid in the polar organic solvent.

2. The measurement method according to claim 1, wherein the polar organic solvent is alcohol.

3. The measurement method according to claim 1, wherein the measurement method is a flow injection analysis method.

4. A measurement apparatus for measuring a content of water or organic acid in a polar organic solvent, comprising:
    as a working electrode, an ISFET electrode, with a membrane made from one of an oxide and a nitride of an element selected from among Groups 3 to 15 metal and metalloid elements being formed on a gate of the ISFET electrode which is sensitive to hydrogen ions, the ISFET electrode configured to detect hydrogen ions in the polar organic solvent; and
    an analyzer for calculating a content of one of water and the organic acid in the polar organic solvent based on a hydrogen ion concentration in the polar organic solvent detected by the ISFET electrode.

5. The measurement apparatus according to claim 4, wherein
    the oxide or the nitride of the elements is selected from the Groups 3 to 15 metal or metalloid elements is $TiO_2$, $Ta_2O_5$ or $Si_3N_4$.

6. The measurement apparatus according to claim 4, wherein
    a body of the ISFET electrode is made from one of metal, ceramics, polyphenyl sulfide, fluorine resin and glass.

7. The measurement apparatus according to claim 4, further comprising a flow cell.

8. The measurement apparatus according to claim 4, wherein
    the ISFET electrode includes a liquid earth mechanism.

* * * * *